United States Patent [19]

Ueda et al.

[11] Patent Number: 5,292,968
[45] Date of Patent: Mar. 8, 1994

[54] PROCESS FOR PRODUCING OVER-BASED ALKALINE EARTH METAL PHENATE

[75] Inventors: Sanae Ueda; Yoshihiro Kojima; Makoto Nishishita; Shinji Yamaoka, all of Saitama, Japan

[73] Assignees: Cosmo Research Institute; Cosmo Oil Co., Ltd., both of Tokyo, Japan

[21] Appl. No.: 22,101

[22] Filed: Feb. 25, 1993

[30] Foreign Application Priority Data

Feb. 26, 1992 [JP] Japan .................................. 4-075252
Aug. 15, 1992 [JP] Japan .................................. 4-238898

[51] Int. Cl.$^5$ ..................... C07C 39/00; C07C 39/235
[52] U.S. Cl. .................................................. 568/716
[58] Field of Search ........................................ 568/716

[56] References Cited

U.S. PATENT DOCUMENTS 4,518,807 5/1985 Hori .................................... 568/716

*Primary Examiner*—Werren B. Lone
*Attorney, Agent, or Firm*—Sughrue, Mion, Zinn, Macpeak & Seas

[57] ABSTRACT

A process for the production of an over based alkaline earth metal phenate (sulfurized, unsulfurized or a mixture thereof), in which the process comprises the steps of: effecting reactions among phenols, dihydric alcohols and an alkaline earth metal reagent (alkaline earth metal oxide or hydroxide or a mixture thereof), or among these compounds further mixed with sulfur and/or water; removing an excess of the dihydric alcohols and at least an excess of water by distillation; and subsequently treating resulting distillation residue with carbon dioxide, wherein the improvement resides in that the carbon dioxide treatment is carried out in the presence of water in an amount of from 0.01 to 1.0 mol per 1 mol of the alkaline earth metal reagent. Preferably, the carbon dioxide treatment is carried out in the presence of 0.1 to 0.7 mol sulfur and 0.1 to 1.0 mol water per 1 mol of the alkaline earth metal reagent.

The process of this invention is industrially advantageous because the alkaline earth metal phenate obtained by the process has a high basicity and an easily handleable low viscosity and is useful as a high quality detergent for a lubricating or fuel oil.

16 Claims, No Drawings

PROCESS FOR PRODUCING OVER-BASED ALKALINE EARTH METAL PHENATE

FIELD OF THE INVENTION

This invention relates to an industrially advantageous process for the production of an alkaline earth metal phenate which has a high basicity and an easily handleable low viscosity and is useful as an alkaline detergent for a lubricating oil or fuel oil.

BACKGROUND OF THE INVENTION

In general, two processes are used for the introduction of sulfur into a phenate: a process in which an alkylphenol is firstly converted into its sulfide from using sulfur chloride or the like and the sulfide is then made into a metal salt; and another process in which sulfurization is carried out using elemental sulfur at the time of metal addition reaction or after metal salt formation. The present invention belongs to the latter sulfurization process. A number of methods for the production of an over-based phenate in which the latter sulfurization process was employed have been reported for a long time, such as a process by which an over-based phenate containing alkaline earth metals in two times or more higher amount than the theoretical amount can be produced with a single metal addition reaction. For example, Hori and Hayashida as disclosed in U.S. Pat. No. 4,123,371 have found that an unexpectedly highly basic alkaline earth metal phenate can be produced by carrying out the above reaction in the presence of excess phenols.

In addition, Hori and Ueda et al. as disclosed in U.S. Pat. No. 4,518,807 have found that conversion ratio of an alkaline earth metal reagent into final product per one reaction can be increased markedly without requiring the use of excess dihydric alcohol by the addition of an appropriate amount of water to a reaction system in which phenols, a dihydric alcohol and an alkaline earth metal reagent or an admixture thereof with sulfur are allowed to react with one another.

Contrary to the generally used processes in which an alkaline earth metal reagent is used in a large excess to an alkylphenol in order to obtain an over-based product, the just described two processes were successful in producing an over-based phenate by the use of a large excess of an alkylphenol against an alkaline earth metal reagent. In consequence, these two processes are advantageous in that kinds of reaction materials to be used can be limited to the minimum.

These processes, however, have disadvantages in that it is extremely difficult to produce an over-based sulfurized phenate having a higher basicity than those of the prior art products and, even if an over-based phenate is produced, the product cannot be handled easily because of its extremely high viscosity. Improvement of the basicity to a higher level than the prior art products and simultaneous decrease in the viscosity will have markedly large economic effects, because not only an over-based phenate can be handled easily but also its amount to be added to lubricating oil and therefore the amount of the expensive alkylphenol can be reduced.

SUMMARY OF THE INVENTION

Taking the aforementioned problems involved in the prior art into consideration, it is the purpose of the present invention to provide an over-based phenate and a process for the production thereof. The phenate according to the present invention has a high basicity and a low viscosity.

With the aim of attaining these objects, the present inventors have conducted intensive studies and found that a phenate having an exceedingly high basicity can be obtained when excess dihydric alcohol is removed by distillation from an intermediate product obtained after (sulfurization and) metal addition reaction and then the resulting intermediate product is reacted with carbon dioxide in the presence of an appropriate amount of water which has been considered to be undesirable as disclosed in U.S. Pat. No. 4,518,807, because of its nature to decrease stability of a final product and prevent normal progress of carbonation reaction when water is present in the reaction system at the time of carbon dioxide treatment of an intermediate product obtained after (sulfurization and) metal addition reactions. The present inventors have found also that viscosity of an over-based sulfurized alkaline earth metal phenate can be decreased sharply and the basicity can be improved when, in addition to the above conditions, the content of sulfur is reduced. The present invention has been accomplished on the basis of these findings which rendered possible production of an over-based alkaline earth metal phenate having a high basicity that cannot be found in the prior art and simultaneously having a low viscosity.

Accordingly, the gist of the present invention resides in a process for the production of an over-based alkaline earth metal phenate (sulfurized, unsulfurized or a mixture thereof, the same rule applies to the following), in which the process comprises the steps of: effecting reactions among phenols, dihydric alcohols and an alkaline earth metal oxide or hydroxide or a mixture thereof (to be referred to as "alkaline earth metal reagent" hereinafter), or among these compounds further mixed with sulfur and/or water; removing an excess amount of the dihydric alcohols and at least an excess amount of water by distillation; and subsequently treating resulting distillation residue with carbon dioxide, wherein the improvement resides in that the carbon dioxide treatment is carried out in the presence of water in an amount of from about 0.01 to 1.0 mol, preferably from about 0.1 to 0.7 mol, per 1 mol of the alkaline earth metal reagent.

Also, as a further preferred embodiment of the present invention, there is provided a process for the production of an over-based alkaline earth metal phenate consisting of the above steps, wherein the carbon dioxide treatment is carried out in the presence of sulfur in an amount of from about 0.1 to 1.0 mol, preferably from about 0.1 to 0.7 mol, more preferably from about 0.2 to 0.5 mol, per 1 mol of the alkaline earth metal reagent, and in the presence of water in an amount of from about 0.1 to 0.7 mol, preferably from 0.2 to 0.5 mol, per 1 mol of the alkaline earth metal reagent.

Other objects and advantages of the present invention will be made apparent as the description progresses.

DETAILED DESCRIPTION OF THE INVENTION

Examples of phenols to be used in the present invention include those which have a hydrocarbon side chain of 4 to 36 carbon atoms, preferably 8 to 32 carbon atoms, such as alkyl, alkenyl, aralkyl or the like group. Illustrative examples of such phenols include those which have a hydrocarbon group such as butyl, amyl, octyl, nonyl, dodecyl, cetyl, ethylhexyl, triacontyl or the like, or a group derived from a petroleum hydrocarbon such as liquid paraffin, wax or an olefinic polymer (for example, polyethylene, polypropylene or polybutene). These phenols may be used alone or as a mixture of two or more thereof. A phenol which becomes liquid at a temperature of about 130° C., preferably at about 120° C., may be used desirably.

With regard to the alkaline earth metal reagent, oxides or hydroxides of alkaline earth metals such as calcium, barium, strontium, magnesium and the like may be used. The alkaline earth metal reagent may be used in an amount of from about 0.001 to 0.99 equivalent per 1 equivalent of phenols. When the amount of the alkaline earth metal reagent is larger than phenols, a product of interest having excellent quality will not be obtained because of the gelation of intermediate products and termination of subsequent reactions. If the amount is too small, not only the product yield per reaction materials would be reduced but also the utility and time required for the recovery of phenols would become large, thus causing disadvantages from the economic point of view.

The dihydric alcohol with a relatively low boiling point, a low viscosity and a high reactivity may be used. Preferably, the dihydric alcohol may have a carbon number of from 2 to 6, with particularly preferred examples including ethylene glycol, propylene glycol and the like. The dihydric alcohol promotes conversion of oil soluble materials by the reaction of phenols with the alkaline earth metal reagent, and a part of the alcohol is incorporated into the final phenate product to construct an over-based phenate. According to the process of the present invention, (sulfurization and) metal addition reaction may be carried out either in the presence or absence of water which is effective in enhancing the reaction. When water is added, the dihydric alcohol may be used in an amount of from about 0.15 to 3.0 mols, preferably from about 0.3 to 1.5 mols, per 1 mol of the alkaline earth metal reagent. When the reaction is carried out without adding water, the dihydric alcohol may be used in an amount of from about 1.0 to 3.0 mols, preferably from about 1.2 to 2.0 mols, per 1 mol of the alkaline earth metal reagent. The amount of the dihydric alcohol if too small would cause reduced the conversion ratio of reaction materials into a product, especially of the alkaline earth metal reagent, and the amount if too large would require too much time and utility for the removal of excess dihydric alcohol from the reaction product, though the metal addition reaction with phenols would progress smoothly.

Sulfur may be used in an amount practically ranging from extremely low level to extremely high level when it is used with the aim of only improving the basicity. In general, it may be used in an amount of about 0.001 to 4.0 mols, preferably from about 0.001 to 3.0 mols, per 1 mol of the alkaline earth metal reagent. The amount of sulfur if too large would cause difficulty in obtaining a basic phenate. The reaction may be effected without using sulfur.

When further improvement of the basicity and reduction of the product viscosity are necessary, sulfur may be used in an amount of from about 0.1 to 1.0 mol, preferably from about 0.1 to 0.7 mol, more preferably from about 0.2 to 0.5 mol, per 1 mol of the alkaline earth metal reagent. Though the product viscosity decreases as the amount of sulfur is reduced, too small an amount will cause reduction of sulfide content and oil solubility of the resulting product. When the amount is too large, not only a product having a high basicity will not be obtained due to decrease in the over-basicity of the product but also viscosity of the product will become considerably high.

When water is added to the reaction system for the purpose of enhancing metal addition reaction of the alkaline earth metal reagent to phenols, not only distilled water but also boiler water, industrial water and the like, as well as water formed by the metal addition reaction, may be used with no particular limitation in their qualities and in any form such as cool water, hot water, steam or the like. Water for use in the enhancement of the metal addition reaction may be supplied to a reactor as it is alone or as a mixture of a part or whole amount of water with other reaction materials such as a phenol, a dihydric alcohol, a higher alcohol and the like. Timing of the addition of water to a reactor is not particularly limited, and it may be added before or after mixing of the entire reaction materials other than water, but preferably within about 1 hour after completion of the mixing of all reaction materials. Amount of water to be added to the reaction system to enhance the metal addition reaction may be in the range of from about 0.01 to 10 mols, preferably from 0.1 to 2.0 mols, per 1 mol of the alkaline earth metal reagent. When the (sulfurization and) metal addition reaction is carried out by adding water from outside to the reaction system, the reaction will progress smoothly and the conversion ratio of the alkaline earth metal reagent into a product, will become high, in comparison with the case of a reaction carried out under the same conditions but without adding water. In consequence, the conversion ratio of the alkaline earth metal reagent into a product will decrease when the amount of water to be added to the reaction system is too small. On the contrary, when the amount of water is too large, it will spoil an advantage of the present invention in terms of the simplification of the distillation step after completion of the reaction.

Control of the amount of water to be coexisted at the time of the carbon dioxide treatment may be effected generally after the completion of steps consisting of: allowing reaction materials including a phenol, a dihydric alcohol and an alkaline earth metal reagent, or a sulfur-added mixture thereof or a water-added mixture thereof to react with one another; completing (sulfurization and) metal addition reaction; and removing water and an excess of dihydric alcohols by distillation. Water to be coexisted at the time of the carbon dioxide treatment may have no particular limitation in its quality and condition, similar to the case of water to be used for the enhancement of the metal addition reaction. Amount of water in the reaction system may be controlled within the range of from about 0.01 to 1.0 mol, preferably from about 0.1 to 0.7 mol, per 1 mol of the alkaline earth metal reagent.

However, when the content of sulfur to be blended is specified as described in the foregoing for the purpose of further improving the basicity and decreasing the product viscosity, water in the reaction system may be controlled within the range of from about 0.1 to 0.7 mol, preferably from about 0.2 to 0.5 mol, per 1 mol of the alkaline earth metal reagent.

When an excess amount of a dihydric alcohol is present in the reaction system, water in the system including added water and formed water by the reaction is entirely removed as a fore-running during removal of the excess dihydric alcohol. In such a case, therefore, it is necessary to add a predetermined amount of water after the removal of excess dihydric alcohol. On the other hand, when the dihydric alcohol is not present in an excess amount in the reaction system, an excess portion of water remained in the system after completion of the reaction, which has been added as a reaction enhancer before the (sulfurization and) metal addition reaction or formed during the reaction, may be removed by distillation, leaving only a predetermined amount of water. When the amount of remained water cannot be judged, it is desirable to add a predetermined amount of water after removing entire amount of the remained water by distillation.

In this instance, it is desirable to keep the dihydric alcohol in the reaction system in an amount of from about 0.15 to 1.5 mols, preferably from about 0.3 to 1.2 mols, per 1 mol of the alkaline earth metal reagent.

Though the product viscosity decreases as the amount of water is increased, too large amount of water will cause reduction of the basicity and oil solubility. In such a case, these problems may be improved by the use of a dispersant such as a sulfonate or the like. When the amount of water is too small, its effect to improve the basicity will not be obtained sufficiently. Though sufficient effect of water may be obtained within the above range, its optimum amount may vary to some extent depending on the amount of sulfur to be used. In particular, it will be effective to decrease the amount of water to be added as the amount of sulfur decreases.

According to the process of the present invention, a diluent or solvent having a proper viscosity (to be referred to as "diluent" hereinafter) may be added to the reaction system in order to effect easy handling of a reaction product or a reaction intermediate. For example, when the recovery of an excess amount of unreacted phenols from a reaction product is carried out by means of distillation in the presence of a diluent having a high boiling point and a proper viscosity, the resulting reaction product can be obtained in a desirable liquid form. In this instance, a portion of the diluent may be distilled off with the distillation of unreacted phenols. In consequence, it is desirable to use a diluent which does not exert influence on the reaction when the recovered unreacted phenols are repeatedly used in the reaction. Preferred examples of the diluent include a paraffinic, naphthenic, aromatic or a mixture of petroleum distillate having a proper viscosity, such as a lubricating oil fraction having a boiling point of from about 220° to 550° C. and a viscosity of from about 2 to 40 cSt at 100° C. Any other organic solvent may also be used as the diluent as long as it shows a lipophilic property and is not influenced on the reaction or the practical use of the final product.

The following describes main steps and operation conditions to be employed in the production process of the over-based phenate of the present invention.

The (sulfurization and) metal addition step is carried out using phenols, dihydric alcohols and an alkaline earth metal reagent, or a sulfur-added mixture thereof or a water-added mixture thereof. The reaction may be carried out at a temperature of from about 60° to 200° C., preferably from about 90° to 190° C., if necessary under a pressure of from 0.1 to 10 atm A.

When sulfur is used, sulfurization reaction occurs simultaneously with the metal addition reaction. Hydrogen sulfide generated during the reaction may or may not be removed from the reaction system. This reaction completes generally within the range of from about 1 to 9 hours.

After completion of the (sulfurization and) metal addition reaction, excess amounts of water and dihydric alcohol are removed from the reaction system by distillation, a predetermined amount of water is located in the system, and then the carbon dioxide treatment step is effected by allowing the resulting intermediate product to react with carbon dioxide at a temperature of from about 50° to 230° C., preferably from 80° to 200° C. If necessary, the thus obtained product is allowed to stand in an atmosphere of carbon dioxide for a period of from several minutes to a little over 10 hours at a temperature of from about 100° to 230° C. under a pressure of from atmospheric to 20 kg/cm$^2$G, preferably from atmospheric to 11 kg/cm$^2$G. The carbon dioxide treatment is effective in further improving properties of the final product as lubricating oil and fuel oil additives, specially in improving solubility and stability of the product in engine oil.

It is possible to incorporate more metals to the reaction product obtained after the carbon dioxide treatment by adding the alkaline earth metal reagent and dihydric alcohol to the reaction product, carrying out (sulfurization and) metal addition reaction again in the aforementioned manner and then repeating the carbon dioxide treatment step one or more times. From the economic point of view, it is preferable to recover a part or most of the unreacted phenols from the reaction product obtained after the carbon dioxide treatment and to use the recovered phenols again as the reaction material. In that case, a distillation residue will be obtained in a desirable liquid form when distillation of the unreacted phenols is carried out in the presence of a usually used diluent such as high boiling point mineral oil. Insoluble materials in the distillation residue may be removed by filtration, centrifugation or the like means before or after the recovery of phenols.

By the coexistence of an appropriate amount of water at the carbon dioxide treatment which is carried out after the (sulfurization and) metal addition reaction, at least a part of water directly takes part in the reaction system and decreases the amount of phenols incorporated into the resulting product, thereby rendering possible considerable increase in the basicity of the product obtained by the process of the present invention in comparison with the case of similar process with no coexistence of water, in spite of the use of a relatively simple process and a small number of reaction materials.

In general, when a detergent such as phenate is added to lubricating oil and the like, the amount of the detergent to be added is calculated based on its total base number. In consequence, increasing of the basicity leads to markedly large economic effects, because the amount of expensive alkylphenol to be used can be reduced.

In addition, the following effects can be obtained by the addition of sulfur within the aforementioned specific blending range together with the introduction of an appropriate amount of water at the time of the carbon dioxide treatment.

(1) A product having a high total base number of 300 mg KOH/g or more can be produced. While prior art product having an easily handleable viscosity has a total base number of about 260 mg KOH/g at the most, the present invention has rendered possible improvement of the total base number by a factor of 15% or more.

(2) Product viscosity can be decreased sharply. A product having a total base number of 300 mg KOH/g or more cannot be obtained easily by the prior art process without reducing the amount of diluent oil to a minimum level which entails considerable increase in the product viscosity. Contrary to this, a product having a total base number of about 300 mg KOH/g having almost the same viscosity as that of the prior product (total base number, about 260 mg KOH/g) can be produced by the use of the process of the present invention. As a matter of course, handling of a product at the time of its addition to lubricating oil and the like can be made easily with the decreasing of the product viscosity.

The following examples are provided to further illustrate the present invention. It is to be understood, however, that the examples are for purpose of illustration only and are not intended as a definition of the limits of the invention.

INVENTIVE EXAMPLE 1

A four-necked flask equipped with a stirrer, a condenser, a nitrogen gas inlet and a thermometer was charged with 2,310 g (10.5 moles) of nonylphenol, 57 g (1.8 moles) of sulfur and 168 g (3.0 moles) of 100% pure calcium oxide, followed by stirring. The resulting suspension was mixed with 306 g (5.1 moles) of ethylene glycol in a stream of nitrogen under normal pressure at 130° C., and the mixture was stirred for 5 hours at 135° C. to effect sulfurization and metal addition reaction. With gradual decrease of pressure in the reaction system, formed water by the reaction, 196.2 g (3.27 moles) of ethylene glycol and a small quantity of nonylphenol were removed by distillation to obtain 2,549.1 g of a distillation residue in a liquid form. The liquid distillation residue thus obtained was found to have a viscosity of 86.21 cSt (at 100° C.), an ethylene glycol content of 0.61 mole/mole Ca, a calcium content of 4.72% by weight and a sulfur content of 2.03% by weight. A 787.3 g portion of the distillation residue was mixed with 5.6 g (0.31 mole; 0.33 mole/mole calcium oxide) of water, and the mixture was put in an autoclave to allow the mixture to absorb carbon dioxide under a pressure of 5 kg/cm$^2$G and at a temperature of 150° C. for a period of 30 minutes. After becoming the pressure 2 kg/cm$^2$G and increasing the temperature to 175° C., carbon dioxide was again introduced into the autoclave until the pressure increased to 5 kg/cm$^2$G, and the contents were allowed to stand for 2 hours to obtain a reaction product solution. In this instance, introduction of carbon dioxide into the autoclave was carried out while measuring its quantity. A 804.0 g portion of the reaction product solution was mixed with 217.9 g of 150 neutral oil as a diluent, and the mixture was filtered to remove 1.10 g of insoluble materials. The thus obtained filtrate was put into a three-necked pear-shaped flask and subjected to distillation under a reduced pressure to remove 12.0 g (0.20 mole) of ethylene glycol and most of unreacted nonylphenol dissolved in the filtrate, thereby obtaining 419.5 g of a distillation residue as a final product. In this instance, the final distillation temperature was 155° C. (1 mmHg). Properties of the final product are shown in Table 1.

COMPARATIVE EXAMPLE 1

A 1,181 g portion of the 2,549.1 g distillation residue obtained after the sulfurization and metal addition reactions in Inventive Example 1 was used as a starting material. Carbon dioxide treatment of the material was carried out in the same manner as described in Inventive Example 1 except that water was not added to the material, 150 neutral oil was added in an amount of 337.0 g and 1.6 g of insoluble materials were removed. In this way, 682.1 g of a final product was obtained, with its properties shown in Table 1.

TABLE 1

| Properties of final products: | Inventive Example 1 | Comparative Example 1 |
|---|---|---|
| Metal addition equivalent ratio (PEQ value)* | 3.83 | 2.26 |
| Viscosity cSt at 100° C. | 72.09 | 150.3 |
| Total base number mg KOH/g | 241 | 225 |
| Ca content wt % | 8.61 | 8.07 |
| S content wt % | 3.03 | 3.01 |

*Gram equivalent ratio of alkaline earth metal per phenol component in the phenate product, which can be used as an estimate of the basicity. Similarly, the total base number (at the same viscosity) can be used as an estimate of the basicity.

COMPARATIVE EXAMPLE 2

A 500 g portion of the 2,549.1 g distillation residue obtained after the sulfurization and metal addition reactions in Inventive Example 1 was used as a starting material. Carbon dioxide treatment of the material was carried out by adding 15.9 g (0.883 mole; 1.50 moles per mole calcium oxide) of water to the material, but the resulting product was hardly filterable and insoluble in paraffinic base oil.

The product obtained in Comparative Example 2 in which an excess of water was added at the time of carbon dioxide treatment was hardly useful from practical point of view. It is evident also that the final product obtained in Inventive Example 1 in which an appropriate amount of water is added at the time of carbon dioxide treatment has an improved PEQ value in comparison with the case of Comparative Example 1 in which water is not added.

INVENTIVE EXAMPLE 2

An autoclave was charged with 660 g (3.0 moles) of nonylphenol, 22.4 g (0.7 mole) of sulfur and 58.4 g (1.0 mole) of 96.0% pure calcium oxide. With stirring, the resulting suspension was mixed with a mixture solution consisting of 33 g (0.55 mole) of ethylene glycol and 18 g (1.0 mole) of water, and the resulting mixture was stirred in a stream of nitrogen for 5 hours at 130° C. under a pressure of 2 kg/cm$^2$G to effect sulfurization and metal addition reaction. In this instance, the mixture solution was maintained in a stream of nitrogen for 30 minutes at 125° C. under normal pressure prior to its use. With gradual decrease of pressure in the reaction system, water and a small amount of ethylene glycol were removed by distillation to obtain 742.6 g of a distillation residue. In this instance, the final distillation temperature was 25° C. (32 mmHg). Water was mainly removed by this distillation step within a relatively short period of time and easily.

The liquid distillation residue thus obtained was found to have a viscosity of 168.3 cSt (at 100° C.), an ethylene glycol content of 0.54 mole/mole Ca, a calcium content of 5.4% by weight and a sulfur content of 2.1% by weight.

The distillation residue thus obtained was mixed with 3.6 g (0.2 mole; 0.2 mole/mole calcium oxide) of water, and the mixture was allowed to absorb carbon dioxide under a pressure of 5 kg/cm$^2$G and at a temperature of 120° C. for a period of 30 minutes. After becoming the pressure 2 kg/cm$^2$G and increasing the temperature to 175° C., carbon dioxide was again introduced into the autoclave until the pressure increased to 5 kg/cm$^2$G, and the contents were allowed to stand for 2 hours to obtain a reaction product solution. The reaction product solution was mixed with 242.3 g of 150 neutral oil as a diluent, and the mixture was filtered to remove 2.1 g of insoluble materials. The thus obtained filtrate was put into a three-necked pear-shaped flask and subjected to distillation under a reduced pressure to remove a portion of ethylene glycol and most of unreacted nonylphenol dissolved in the filtrate, thereby obtaining 472.3 g of a distillation residue as a final product. In this instance, the final distillation temperature was 155° C. (1 mmHg). Product conversion ratios of the reaction materials and properties of the final product are shown in Table 2.

In addition, a portion of the final product was subjected to a column chromatography using silica gel as an adsorbent and n-hexane as a substitution agent to isolate an active component in the form of pale yellow powder. The thus isolated active component was hydrolyzed with an excess amount of 1N sulfuric acid aqueous solution and the resulting oil layer was analyzed by liquid chromatography to find that 3.8 mol% of the active component-constituting nonylphenol was nonylsalicylic acid.

INVENTIVE EXAMPLE 3

The steps before the carbon dioxide treatment in Inventive Example 1 were repeated to obtain 2,551.0 g of a distillation residue in a liquid form. A 859.2 g portion of the distillation residue was mixed with 12.1 g (0.67 mole; 0.66 mole/mole calcium oxide) of water, and the mixture was put in an autoclave to allow the mixture to absorb carbon dioxide under a pressure of 5 kg/cm²G and at a temperature of 120° C. for a period of 30 minutes. After decreasing the pressure to 2 kg/cm²G and increasing the temperature to 155° C., carbon dioxide was again introduced into the autoclave until the pressure increased to 5 kg/cm²G, and the contents were allowed to stand for 2 hours to obtain 910.9 g of a reaction product solution. A 890.9 g portion of the reaction product solution was mixed with 217.9 g of 150 neutral oil as a diluent, and the mixture was filtered to remove 1.10 g of insoluble materials. The thus obtained filtrate was put into a three-necked pear-shaped flask and subjected to distillation under a reduced pressure to remove 18.6 g (0.31 mole) of ethylene glycol and most of unreacted nonylphenol dissolved in the filtrate, thereby obtaining 428.9 g of a distillation residue as a final product. In this instance, the final distillation temperature was 155° C. (1 mmHg). Product conversion ratios of the reaction materials and properties of the final product are shown in Table 2.

When the final product was analyzed in the same manner as described in Inventive Example 2, it was found that 3.1 mol% of the active component-constituting nonylphenol was nonylsalicylic acid.

TABLE 2

|  | Inventive Example 2 | Inventive Example 3 |
|---|---|---|
| Product conversion ratio of reaction materials: | | |
| CaO % | 97.9 | 98.8 |
| NP* % | 21.1 | 12.5 |
| S % | 62.8 | 61.5 |
| EG** % | 71.1 | 15.9 |
| CO₂ % | 16.7 | 78.5 |
| Properties of final products: | | |
| Metal addition equivalent ratio (PEQ value) | 3.09 | 4.53 |
| Viscosity cSt at 100° C. | 89.28 | 79.48 |
| Total base number mg KOH/g | 233 | 255 |
| Ca content wt % | 8.31 | 9.16 |
| S content wt % | 2.99 | 2.73 |
| Reacted CO₂ content wt % | 5.66 | 7.06 |

(Note): *NP, nonylphenol; **EG, ethylene glycol

It is evident that the final products obtained in Inventive Example 2 in which water is coexisted in an amount of 0.2 mole per mole calcium oxide at the time of the carbon dioxide treatment and Inventive Example 3 in which 0.66 mole of water is coexisted have markedly improved PEQ values in comparison with the results of Comparative Example 1.

INVENTIVE EXAMPLE 4

A four-necked flask similar to the one used in Inventive Example 1 was charged with 880 g (4.0 moles) of nonylphenol and 56.1 g (1.0 mols) of calcium oxide, followed by stirring. The resulting suspension was mixed with a mixture solution consisting of 36 g (0.6 mole) of ethylene glycol and 19.8 g (1.1 moles) of water, and the resulting mixture was stirred for 5 hours at 130° C. to effect metal addition reaction. In this instance, the mixture solution was maintained in a stream of nitrogen for 30 minutes at 125° C. under normal pressure prior to its use. With gradual decrease of pressure in the reaction system, water and a small amount of ethylene glycol were removed by distillation to obtain 953.5 g of a distillation residue in a liquid form. The thus obtained distillation residue was transferred into an autoclave and mixed with 7.2 g (0.4 mole; 0.4 mole/mole calcium oxide) of water, and the mixture was allowed to absorb carbon dioxide under a pressure of 11 kg/cm²G and at a temperature of 120° C. for a period of 30 minutes. After becoming the pressure 5 kg/cm²G and increasing the temperature to 175° C., the contents were allowed to stand for 2 hours to obtain a reaction product solution. The reaction product solution was then mixed with 237.4 g of 150 neutral oil, and the mixture was filtered to remove 2.8 g of insoluble materials. The thus obtained filtrate was put into a three-necked pear-shaped flask and subjected to distillation under a reduced pressure to remove a portion of unreacted ethylene glycol and most of unreacted nonylphenol dissolved in the filtrate, thereby obtaining 411.9 g of a distillation residue as a final product. In this instance, the final distillation temperature was 157° C. (1.5 mmHg). Product conversion ratios of the reaction materials and properties of the final product are shown in Table 3.

COMPARATIVE EXAMPLE 3

A 463.4 g portion of a final product was obtained by repeating the process of Inventive Example 4 except that water was not added and the carbon dioxide treatment was carried out. Product conversion ratios of the reaction materials and properties of the final product are shown in Table 3.

TABLE 3

|  | Inventive Example 4 | Comparative Example 3 |
|---|---|---|
| Product conversion ratio of reaction materials: | | |
| CaO % | 97.5 | 97.6 |
| NP* % | 12.7 | 16.4 |

TABLE 3-continued

|  | Inventive Example 4 | Comparative Example 3 |
|---|---|---|
| EG** % | 16.4 | 61.5 |
| $CO_2$ % | 72.3 | 49.7 |
| Properties of final products: | | |
| Metal addition equivalent ratio (PEQ value) | 3.83 | 2.97 |
| Viscosity cSt at 100° C. | 106.3 | 88.34 |
| Total base number mg KOH/g | 260 | 231 |
| Ca content wt % | 9.30 | 8.22 |
| Reacted $CO_2$ content wt % | 6.80 | 4.22 |

(Note): *NP, nonylphenol; **EG, ethylene glycol

It is evident from these results that, even in the absence of sulfur, PEQ value of the final product obtained in Inventive Example 4 in which the carbon dioxide treatment was carried out in the present of water is markedly higher than that of the final product of Comparative Example 3 in which the carbon dioxide treatment was carried out in the absence of water. It is evident also that the product of Inventive Example 4 obtained without using sulfur has almost the same PEQ value as those of the final products obtained in Inventive Examples 1, 2 and 3 in which sulfur is used.

INVENTIVE EXAMPLE 5

A 1 liter capacity autoclave equipped with a stirrer, a nitrogen gas inlet and a thermometer was charged with 83.57 g (2.1 moles) of 94.39% pure dodecylphenol, 42.14 g (0.7 mole) of 93.2% pure calcium oxide and 6.74 g (0.21 mole; 0.3 mole/mole calcium oxide) of sulfur, followed by stirring. The resulting suspension was mixed with 65.21 g (1.05 moles) of ethylene glycol at 125° C., and the mixture was stirred for about 3.0 hours at 130° C. under a pressure of about 3.0 kg/cm²G in a closed condition. With gradual decrease of pressure in the reaction system, formed water by the reaction, a portion of unreacted ethylene glycol and a small quantity of dodecylphenol were removed by distillation to obtain 659.0 g of a distillation residue in a liquid form. In this instance, the final distillation temperature was 140° C. (10 mmHg). A 659.0 g portion of the distillation residue was mixed with 5.04 g (0.28 mole; 0.4 mole/mole calcium oxide) of water under a reduced pressure, and the mixture was allowed to absorb carbon dioxide at a temperature of 150° C. for a period of 30 minutes. In this instance, introduction of carbon dioxide into the autoclave was carried out at a rate of 0.315 l/min. After increasing the temperature to 175° C., carbon dioxide was again introduced into the autoclave until the pressure increased to 5.0 kg/cm²G, and the contents were allowed to stand for 2 hours to obtain 688.0 g of a reaction product. A 688.0 g portion of the reaction product was mixed with 117.8 g of 150 neutral oil as a diluent. A 732.18 g portion of the resulting mixture was put into a 1 liter capacity three-necked pear-shaped flask and subjected to distillation under a reduced pressure to remove a small amount of ethylene glycol and most of unreacted dodecylphenol, thereby obtaining 207.8 g of a distillation residue. In this instance, the final distillation temperature was 230° C. (2.5 mmHg). Thereafter, the thus obtained distillation residue was diluted with a large amount of hexane, 5.21 g of insoluble materials were removed from the diluted sample by centrifugation and then the large volume hexane was removed by distillation to obtain 194.3 g of a final product. Properties of the final product are shown in Table 4.

INVENTIVE EXAMPLE 6

A 1 liter capacity autoclave equipped with a stirrer, a nitrogen gas inlet and a thermometer was charged with 583.57 g (2.1 moles) of 94.39% pure dodecylphenol, 42.14 g (0.7 mole) of 93.2% pure calcium oxide and 8.99 g (0.28 mole; 0.4 mole/mole calcium oxide) of sulfur, followed by stirring. The resulting suspension was mixed with 65.21 g (1.05 moles) of ethylene glycol at 125° C., and the mixture was stirred for about 3.0 hours at 130° C. under a pressure of about 3.0 kg/cm²G in a closed condition. With gradual decrease of pressure in the reaction system, formed water by the reaction, a portion of unreacted ethylene glycol and a small quantity of dodecylphenol were removed by distillation to obtain 646.3 g of a distillation residue in a liquid form. In this instance, the final distillation temperature was 140° C. (10 mmHg). A 646.3 g portion of the distillation residue was mixed with 5.04 g (0.28 mole; 0.4 mole/mole calcium oxide) of water under a reduced pressure, and the mixture was allowed to absorb carbon dioxide at a temperature of 150° C. for a period of 30 minutes. In this instance, introduction of carbon dioxide into the autoclave was carried out at a rate of 0.315 l/min. After increasing the temperature to 175° C., carbon dioxide was again introduced into the autoclave until the pressure increased to 5.0 kg/cm²G, and the contents were allowed to stand for 2 hours to obtain 680.7 g of a reaction product. A 680.7 g portion of the reaction product was mixed with 117.8 g of 150 neutral oil as a diluent. A 657.8 g portion of the resulting mixture was put into a 1 liter capacity three-necked pear-shaped flask and subjected to distillation under a reduced pressure to remove a small amount of ethylene glycol and most of unreacted dodecylphenol, thereby obtaining 192.4 g of a distillation residue. In this instance, the final distillation temperature was 225° C. (2 mmHg). Thereafter, the thus obtained distillation residue was diluted with a large amount of hexane, 7.49 g of insoluble materials were removed from the diluted sample by centrifugation and then the large amount of hexane was removed by distillation to obtain 180.5 g of a final product. Properties of the final product are shown in Table 4.

COMPARATIVE EXAMPLE 4

A final product was obtained with a yield of 192.5 g by repeating the process of Inventive Example 5 except that the amount of sulfur was changed to 15.73 g (0.49 mole; 0.7 mole/mole calcium oxide) and the amount of water was changed to 6.30 g (0.35 mole; 0.5 mole/mole calcium oxide). Properties of the final product are shown in Table 4.

COMPARATIVE EXAMPLE 5

A final product was obtained with a yield of 262.1 g by repeating the process of Inventive Example 5 except that the amount of sulfur was changed to 8.99 g (0.28 mole; 0.4 mole/mole calcium oxide) and water was not added. Properties of the final product are shown in Table 4.

TABLE 4

| Properties of final products: | Inventive Ex. | | Comparative Ex. | |
|---|---|---|---|---|
|  | 5 | 6 | 4 | 5 |
| Viscosity cSt at 100° C. | 653 | 622 | 4432 | 539 |
| Total base value mg KOH/g | 342 | 315 | 326 | 265 |
| Ca content wt % | 11.8 | 11.0 | 11.4 | 9.39 |
| S content wt % | 2.60 | 3.04 | 4.27 | 2.69 |

TABLE 4-continued

| Properties of final products: | Inventive Ex. | | Comparative Ex. | |
|---|---|---|---|---|
| | 5 | 6 | 4 | 5 |
| Reacted $CO_2$ content wt % | 9.51 | 8.63 | 8.57 | 6.31 |

It is evident from the results shown in the above table that the final products obtained in Inventive Examples 5 and 6 by respectively blending 0.3 mole and 0.4 mole of sulfur per 1 mole of calcium oxide have markedly decreased viscosities in comparison with the case of Comparative Example 4 in which sulfur is used in an amount of 0.7 mole per 1 mole calcium oxide. In addition, the final products obtained in Inventive Examples 5 and 6 have total base numbers of more than 300 mg KOH/g which are about 20% or more higher than the final product of Comparative Example 5 in which water is not used, in spite of almost the same viscosity.

While the invention has been described in detail and with reference to specific embodiments thereof, it will be apparent to one skilled in the art that various changes and modifications can be made therein without departing from the spirit and scope thereof.

What is claimed is:

1. A process for producing an over based alkaline earth metal phenate in a sulfurized or unsulfurized form or as a mixture thereof, in which said process comprises the steps of: effecting reactions among phenols having a hydrocarbon side chain of 4 to 36 carbon atoms, dihydric alcohols having a carbon number of from 2 to 6 and an alkaline earth metal oxide or hydroxide or a mixture thereof (referred to as "alkaline earth metal reagent" hereinafter), or among said compounds further mixed with one or both of sulfur and water at a temperature of from 60° to 200° C.; removing an excess amount of the dihydric alcohols and at least an excess amount of water by distillation; and subsequently treating resulting distillation residue with carbon dioxide at a temperature of from about 50° to 230° C., wherein the improvement resides in that said carbon dioxide treatment is carried out in the presence of water in an amount of from about 0.01 to 1.0 mol per 1 mol of said alkaline earth metal reagent.

2. The process according to claim 1, wherein said carbon dioxide treatment is carried out in the presence of water in an amount of from about 0.1 to 0.7 mol per 1 mol of said alkaline earth metal reagent.

3. The process according to claim 1, wherein said alkaline earth metal reagent is used in an amount of from about 0.001 to 0.99 equivalent per 1 equivalent of phenols.

4. The process according to claim 1, 2 or 3, wherein sulfur is used in an amount of from about 0.001 to 4.0 mols per 1 mol of said alkaline earth metal reagent.

5. The process according to claim 1, 2 or 3, wherein sulfur is used in an amount of from about 0.001 to 3.0 mols per 1 mol of said alkaline earth metal reagent.

6. The process according to claim 1, 2, or 3, wherein sulfur is not used.

7. A process for producing an over based alkaline earth metal phenate in a sulfurized or unsulfurized form or as a mixture thereof, in which said process comprises the steps of: effecting reactions among phenols having a hydrocarbon side chain of 4 to 36 carbon atoms, dihydric alcohols having a carbon number of from 2 to 6 and an alkaline earth metal oxide or hydroxide or a mixture thereof (referred to as "alkaline earth metal reagent" hereinafter), or among said compounds further mixed with one or both of sulfur and water at a temperature of from 60° to 200° C.; removing an excess amount of the dihydric alcohols and at least an excess amount of water by distillation; and subsequently treating resulting distillation residue with carbon dioxide at a temperature of from about 50° to 230° C., wherein the improvement resides in that said carbon dioxide treatment is carried out in the presence of water in an amount of from about 0.1 to 0.7 mol per 1 mol of said alkaline earth metal reagent.

8. The process according to claim 7, wherein said carbon dioxide treatment is carried out in the presence of water in an amount of from about 0.2 to 0.5 mol per 1 mol of said alkaline earth metal reagent.

9. The process according to claim 7, wherein said alkaline earth metal reagent is used in an amount of from about 0.001 to 0.99 equivalent per 1 equivalent of phenols.

10. The process according to claim 7, 8 or 9, wherein sulfur is used in an amount of from about 0.1 to 1.0. mol per 1 mol of said alkaline earth metal reagent.

11. The process according to claim 7, 8 or 9, wherein sulfur is used in an amount of from about 0.1 to 0.7 mol per 1 mol of said alkaline earth metal reagent.

12. The process according to claim 7, 8 or 9, wherein sulfur is used in an amount of from about 0.2 to 0.5 mol per 1 mol of said alkaline earth metal reagent.

13. The process according to claim 1 or 7, wherein said dihydric alcohol is used in an amount of from about 1.0 to 3.0 mols per 1 mol of said alkaline earth metal reagent in the metal addition or sulfurization and metal addition reaction.

14. The process according to claim 1 or 7, wherein water is added in an amount of from about 0.01 to 10 mols per 1 mol of said alkaline earth metal reagent in the metal addition or sulfurization and metal addition reaction.

15. The process according to claim 14, wherein said dihydric alcohol is used in an amount of from about 0.15 to 3.0 mols per 1 mol of said alkaline earth metal reagent in the metal addition or sulfurization and metal addition reaction.

16. The process according to claim 1 or 7, wherein said dihydric alcohol is used in an amount of from about 0.15 to 1.5 mols per 1 mol of said alkaline earth metal reagent in the carbon dioxide treatment.

* * * * *